United States Patent [19]
Kubota

[11] Patent Number: 6,133,995
[45] Date of Patent: Oct. 17, 2000

[54] PARTICLE MEASURING APPARATUS

[75] Inventor: Fumio Kubota, Nishinomiya, Japan

[73] Assignee: Sysmex Corporation, Hyogo, Japan

[21] Appl. No.: 09/070,811

[22] Filed: May 1, 1998

[30] Foreign Application Priority Data

May 9, 1997 [JP] Japan ................................. 9-119846
May 13, 1997 [JP] Japan ................................. 9-122473

[51] Int. Cl.$^7$ .................................................. G01N 21/00
[52] U.S. Cl. ...................... 356/73; 356/337; 422/82.05; 436/63
[58] Field of Search ........................ 356/72, 73, 432, 356/39, 337; 422/82.05; 436/63

[56] References Cited

U.S. PATENT DOCUMENTS

| | | |
|---|---|---|
| 5,679,575 | 10/1997 | Kubota et al. . |
| 5,719,666 | 2/1998 | Fukuda et al. ............................. 356/73 |
| 5,731,867 | 3/1998 | Katayama ................................. 356/73 |
| 5,757,476 | 5/1998 | Nakamoto et al. ....................... 356/73 |
| 5,824,269 | 10/1998 | Kosaka et al. ............................ 356/73 |

FOREIGN PATENT DOCUMENTS 1-308964  2/1989  Japan .
8-178826  7/1996  Japan .

OTHER PUBLICATIONS

"Japan Internal Medicine Journal" "Platelet Function Test and Problems Thereof", Tsukada Toshiyasu, pp. 822–827.

*Primary Examiner*—Robert H. Kim
*Assistant Examiner*—Zandra V. Smith

[57] ABSTRACT

A particle measuring apparatus includes a characteristic parameter extracting device for extracting a plurality of characteristic parameters from each particle in a sample, and a distribution diagram preparing device for preparing a first distribution diagram on the basis of the extracted characteristic parameters. It further includes a first separating device for separating a cluster including target particles from others on the prepared first distribution diagram. In addition, a discriminating device is included for setting a specified discrimination standard for the separated cluster including the target particles and for judging whether the particles in the cluster are target particles or non-target particles on the basis of the discrimination standard. Finally, a counting device is included for counting the number of the target particles on the basis of a discrimination result of the discriminating device.

36 Claims, 11 Drawing Sheets

SCATTERGRAM (C)

SCATTERGRAM (D)

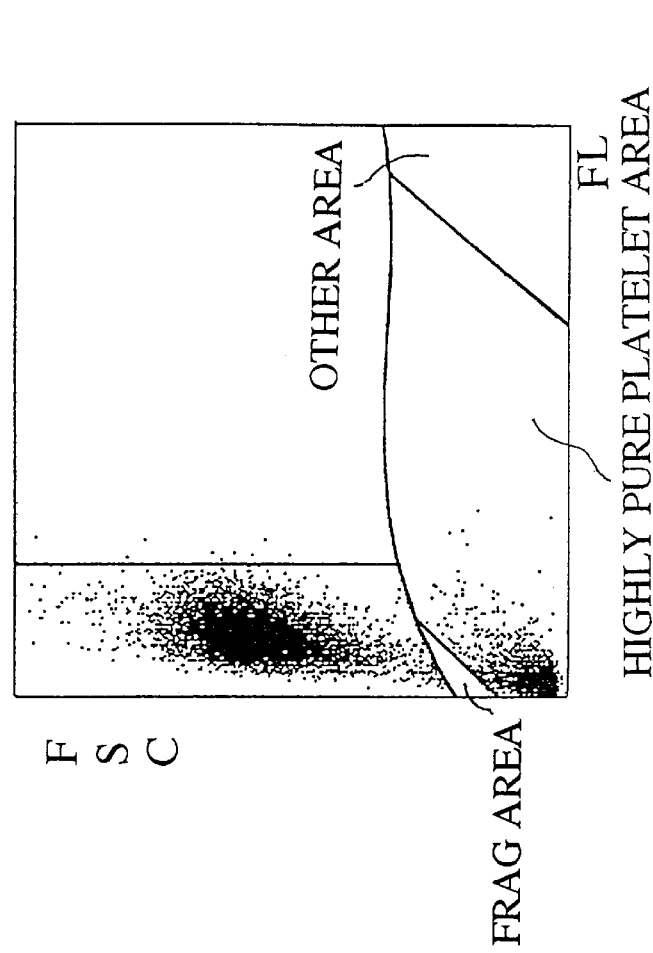
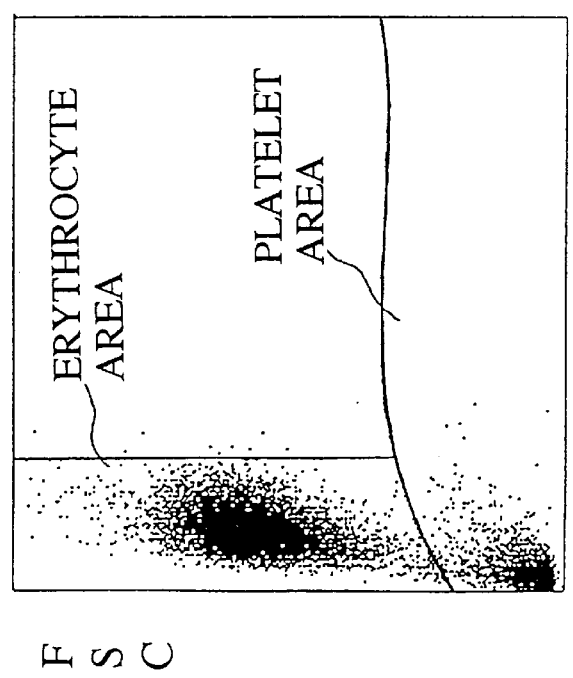

PARTICLE MEASURING APPARATUS

BACKGROUND OF THE INVENTION

1. Field of the Invention

The present invention relates to a particle measuring apparatus, in particular, to a particle measuring apparatus capable of distinguishing target particles in a sample from similar non-target particles for detection and counting. The apparatus is useful in, for example, accurately detecting and counting platelets and aggregations of platelets.

2. Description of the Related Art

Hitherto, counting of the number of particles, such as erythrocytes, leukocytes or platelets, or analysis of the particles has been carried out by obtaining an electrical or optical characteristic parameter with a flow cytometer.

A platelet function test is conducted to test a drop or a rise in the function of platelets. The platelet function test includes various tests such as a platelet adhesion test and a platelet releasing test. Among them, a platelet aggregation test has been frequently carried out, which is for inspecting aggregation of platelets.

In the platelet aggregation test, there has been hitherto used an absorbance method of measuring the degree of platelet aggregation in platelet rich plasma (PRP) as a change in absorbance (Tsukada Toshiyasu, PLATELET FUNCTION TEST AND PROBLEMS THEREOF, Japan Internal Medicine Journal, Vol. 80, No. 6, pp. 822–827, Jun. 10, 1991). This absorbance method comprises adding an aggregation-inducing agent into a given amount of the PRP and measuring the degree of light-shielding (absorbance) caused by aggregations of platelets. It has been used to detect a relatively large aggregation (in which about several hundreds of a single platelet are aggregated).

On the other hand, there are cases where the number of platelets is below several ten thousands/$\mu$L in sudden thrombocytopenia or the like. Also, the number of platelets decreases to a non-measurable level at the time of chemotherapy or bone marrow transplant. When the number of platelets decreases, it is necessary to perform platelet transfusion or administration of hematopoietics. As a judgment standard for the above treatment, the number of platelets is used. Thus, it is extremely important to obtain the number of platelets accurately, especially when the number of platelets is at a low level.

The factors for causing the decrease in the measurement accuracy of the number of platelets may be, for example, particle components such as dusts, bacteria and air bubbles, or appearance of electric noises. These factors will be hereafter referred to as "background noise". For example, particle components may be mingled into a sheath liquid immediately after exchanging sheath liquids. These "background noise" may possibly generate signals similar to signals from platelets and are erroneously counted to show an untrue, high value about the number of platelets.

With respect to the platelet aggregation test, it is known in clinical medicine that platelet function rises in thrombotic diseases such as arteriosclerosis, hyperliperia, diabetes and hypertension, which are adult diseases. It is desired that a so-called thrombus preparing state, which is the state before turning to a thrombus, is discovered at an early stage.

In this thrombus preparing state, a feeble aggregation of platelets (aggregation of several platelets) appear at the initial stage, and consequently a measuring method for detecting feeble aggregations is necessary. In developing an anti-platelet agent or in a safety test for developing a certain medicine, it is desired to detect a feeble aggregation.

In using an anti-coagulation agent, aggregations of platelets may also appear depending on a specimen. Appearance of platelet aggregations makes it impossible to count the number of platelets accurately, and results in an untrue, low or high value about the number of platelets.

According to prior flow cytometers, light is applied to a fine sample stream containing target particles so as to measure information of light from each particle (for example, the intensity of forward scattered light and the intensity of fluorescence), thereby counting the number of the object particles and analyzing them.

For example, a two-dimensional scattergram (two-parameter scattergram) is prepared, using the obtained forward scattered light intensity (FSC) and fluorescence intensity (FL) as characteristic parameters, and then various analyzing treatments are conducted on the basis of the scattergram to separate particle groups from each other and to count the number of particles. For example, an erythrocyte and a platelet are different from each other in their sizes and shapes and consequently they can be separated into clearly different clusters on the scattergram.

A reticulated platelet has a relatively high RNA content among platelets. It is known that the number of reticulated platelets decreases in the case of diseases such as aplastic anemia and acute myelogeneous leukemia. Accordingly, in the case of blood diseases, it is considered to be useful as an indicator of platelet creation in the bone marrow that reticulated platelets are counted and analyzed.

In such a manner as above, the number of platelets can be counted by use of the two-dimensional scattergram (two-parameter scattergram) prepared by means of a flow cytometer. It has been found, by a measuring apparatus (FIC) for capturing images of particles in a sample stream which is made very fine by the flow cytometer, that particles different from platelets, such as fragmented erythrocytes, are present near the cluster of platelets obtained on the two-dimensional scattergram (two-parameter scattergram). A fragmented erythrocyte is a fragment of an erythrocyte, i.e., a torn-off erythrocyte. When non-platelet particles similar to platelets, such as fragmented erythrocytes, are counted as platelets, the number of platelets cannot be calculated accurately. Also, it has been found that the platelet area on the two-dimensional scattergram (two-parameter scattergram) embraces fragmented leukocytes (including eucaryocytes). Also, this results in an error count of platelets.

SUMMARY OF THE INVENTION

The present invention provides a particle measuring apparatus comprising: a characteristic parameter extracting means for extracting a plurality of characteristic parameters from each particle in a sample; a distribution diagram preparing means for preparing a first distribution diagram on the basis of the extracted characteristic parameters; a first separating means for separating a cluster including target particles from others on the prepared first distribution diagram; a discriminating means for setting a specified discrimination standard for the separated cluster including the target particles and judging whether the particles in the cluster are target particles or non-target particles on the basis of the discrimination standard; and a counting means for counting the number of the target particles on the basis of a discrimination result of the discriminating means.

The invention makes it possible to count target particles accurately on the basis of a discrimination standard from a cluster of particles distributed on a distribution diagram prepared based on the characteristic parameters of the particles.

BRIEF EXPLANATION OF THE DRAWINGS

FIG. 11(a) shows an example of a scattergram of a specimen in which fragmented erythrocytes appear according to the invention.

FIG. 11(b) shows an example of a scattergram of a specimen in which fragmented erythrocytes appear according to the invention.

DESCRIPTION OF THE PREFERRED EMBODIMENTS

Figure 1:
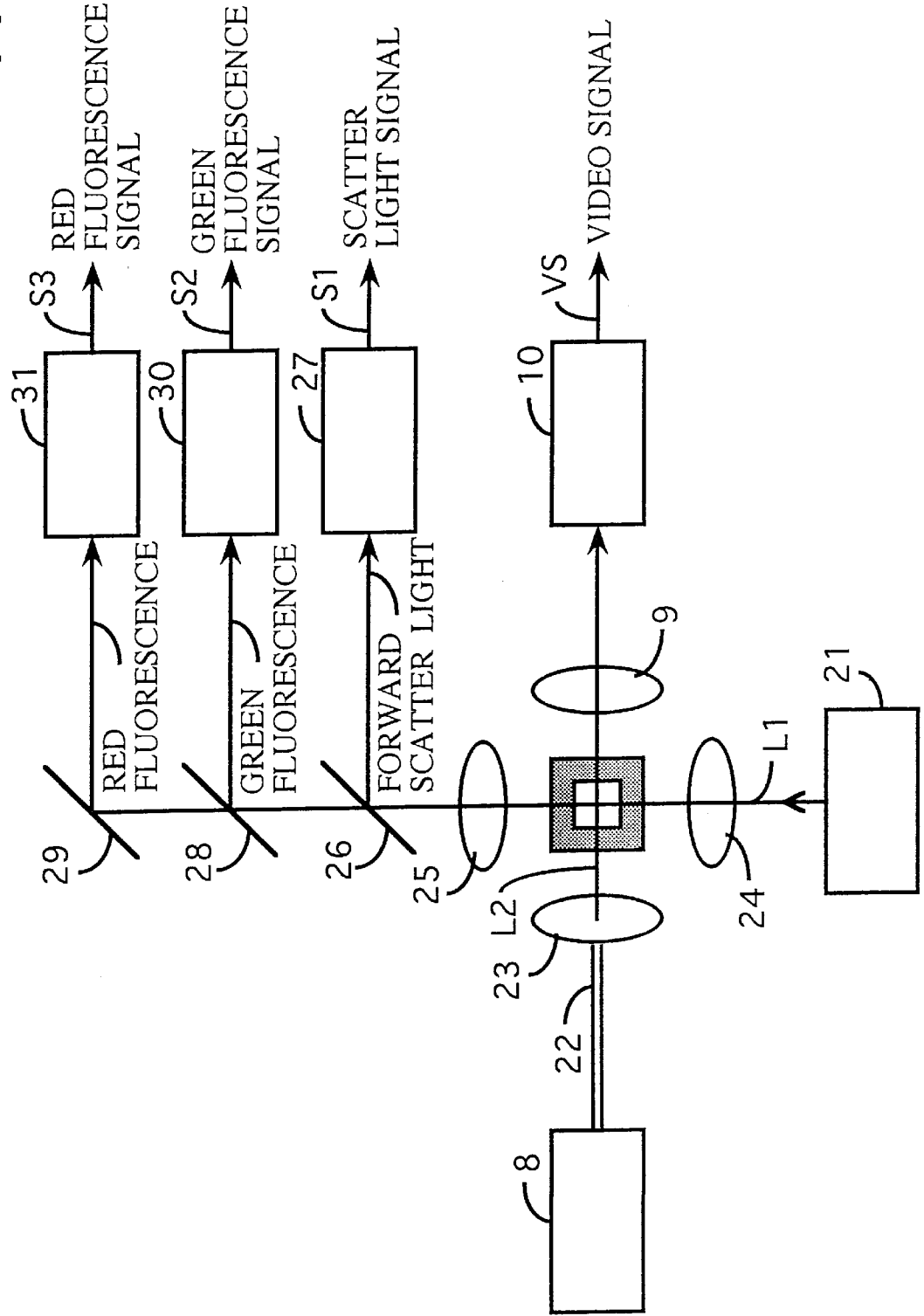
FIG. 1 shows a structure of an optical system in a measuring apparatus according to the present invention.

The present invention will be described below in detail, on the basis of embodiments illustrated in the attached drawings. The invention is not limited to these embodiments.

At first, elements and steps characterizing the present invention will be explained.

The particle to be measured by the present invention is principally a blood corpuscle or a cell contained in blood or urine, but may be a microorganism such as a yeast fungus or a lactic acid bacterium. In particular, a platelet or an aggregation of platelets contained in blood is measured by the invention.

In order to classify the type of blood corpuscle or cell, substances such as particles or nucleic acid in the cell are often reacted with a specific fluorescent agent, and the resultant fluorescent intensity is measured.

The fluorescent agent which may be used, in particular for discriminating a platelet from an erythrocyte or a leukocyte includes Auramine O, Acridine Orange, Propidium iodide, Ethydium bromide, Hoechst 33342, Pyronine Y, and Rhodamine 123. Such a fluorescent agent can be used to measure fluorescent intensity from aggregations of platelets contained in blood appropriately.

The particle measuring apparatus of the present invention principally includes: a characteristic parameter extracting means for extracting a plurality of characteristic parameters from each particle in a sample; a distribution diagram preparing means for preparing a first distribution diagram on the basis of the extracted characteristic parameters; a first separating means for separating a cluster including target particles from others on the prepared first distribution diagram; a discriminating means for setting a specified discrimination standard for the separated cluster including the target particles and judging whether the particles in the cluster are target particles or non-target particles on the basis of the discrimination standard; and a counting means for counting the number of the target particles on the basis of a discrimination result of the discriminating means.

The particle measuring apparatus of the present invention may further comprise a second separating means for finely separating the cluster including the target particles into a plurality of clusters on the first distribution diagram, wherein the distribution diagram preparing means prepares a second distribution diagram for each of the finely separated clusters, and the discriminating means discriminates a particle type for at least one cluster among the plurality of clusters.

The characteristic parameter extracting means may be a means for extracting the characteristic parameters of the particle electrically or optically.

For example, the characteristic parameter extracting means may comprise a sheath flow cell for forming a fine sample stream in which a sample liquid containing particles is surrounded by a sheath liquid, a light applying means for applying light to the sample liquid made into the fine stream, a detecting means for detecting the light scattered by the particles to output electric signals, and a calculating means for calculating the characteristic parameters of the particles from the detected light.

The sheath flow cell is a tool for making it possible to form a fine stream of a sample liquid by a fluid mechanical effect originating from surrounding the sample liquid containing particles with a sheath liquid and letting the surrounded sample liquid flow. As the sheath flow cell, any known one may be used.

The light applying means may be a continuous light source for continuously applying light, such as a laser, a halogen lamp or a tungsten lamp. The detecting means may be one for carrying out electrical detection or optical detection. For example, there is used a light detecting means for detecting particles irradiated by the light applying means optically and then outputting an electrical signal indicating the intensity of scattered light or fluorescence from the particles. The light detecting means may be, for example, a photodiode, a phototransistor or a photomultiplier tube.

The electrical signal outputted from the detecting means is A/D converted and is stored in a memory such as a RAM, as a characteristic parameter of particles, e.g., for the purpose of subsequent counting treatment.

The extracted characteristic parameter may be, for example, scattered light signal intensity, fluorescence signal intensity, scattered light signal pulse width, or fluorescence signal pulse width.

If necessary, the apparatus of the invention may include an image capturing means for capturing images of the particles. The image capturing means is usually a video camera for capturing a two-dimensional image, but may be an image intensifier for intensifying a feeble fluorescent image. The image intensifier may have a shutter.

It is preferred that a light source for irradiating a sample stream is disposed to capture images of the particles. This light source may be a continuous light source for applying light continuously, such as a laser, a halogen lamp or a tungsten lamp, or an intermittent light source for applying light intermittently, such as a pulse laser (for example, 7000 series manufactured by Spectra-Physics) or a multistrobe (for example, DSX series manufactured by Sugawara Institute Co., Ltd.).

When the continuous light source is used to capture images of the particles, it is in generally preferable to use it, as an intermittent light source, by combining it with a light shutter. The light shutter may be, for example, a known acousto-optic modulator, or a known electro-optic modulator. Preferably, the light source and the image capturing means are disposed to sandwich the sheath flow cell, light from the light source is applied on the sample stream perpendicularly, and the image capturing means is disposed on the axis of the light.

The distribution diagram preparing means, the separating means, the discriminating means and the counting means in the invention may be composed of a microcomputer comprising a CPU, a ROM, a RAM, a timer, an I/O interface and the like. The CPU is operated in accordance with the procedure of a program stored in, e.g., the RAM to perform the function of each of the devices.

The distribution diagram preparing means is one for preparing a distribution diagram on the basis of two characteristic parameters. This distribution diagram is usually referred to as a two-dimensional scattergram (two-parameter scattergram). The two-dimensional scattergram (two-parameter scattergram) is prepared by plotting points corresponding to the respective particles on, e.g., a diagram in which the vertical axis shows forward scattered light signal intensity (FSC), and the horizontal axis shows fluorescence intensity (FL).

The intensity in each of the axes in the two-dimensional scattergram (two-parameter scattergram) is represented by intensity (channel) relative to the maximum sensitivity of a photodiode, the sensitivity being 255 channels.

A two-dimensional scattergram (two-parameter scattergram) may also be prepared on a diagram in which the vertical axis shows forward scattered light signal intensity of (FSC) and the horizontal axis shows forward scattered light pulse width (FSW). In general, the forward scattered light signal intensity (FSC), the forward scattered light pulse width (FSW) and the fluorescence intensity (FL) represent the size of a particle, the length of a particle and the RNA content of a particle, respectively.

When the distribution diagram is prepared, a cluster is generally formed for each type of particles. The distribution diagram is separated into respective areas for clusters of the respective particles in a statistical manner. The "two-dimensional distribution (two-parameter distribution) separating method" may be used which is disclosed in Japanese Laid-Open Patent Application JP-A-1-308964.

A cluster of particles separated by the separating means occasionally shows a distribution having a specific shape. For example, the cluster may be distributed to be lined up on a specific straight line or curve. When the cluster of a certain type of particles is distributed to be lined up on a specific curve on the distribution diagram, the specific curve is referred to as an estimation curve or a discrimination curve. In other words, the discrimination standard for discriminating the particles is given as a function on the distribution diagram.

For example, the cluster of platelets shown by forward scattered light signal intensity (FSC) and forward scattered light pulse width is lined up on an estimation curve represented by a function of $sin^2 X$, as will be described later. A means for setting up this estimation curve is called an estimating means.

The discriminating means can discriminate particles present in an area positioned at a distance away from the cluster lined up on the estimation curve as specific particles which are to be observed (target particles). In another case, they may be discriminated as specific particles which are not to be observed (non-target particles).

The distribution operating means is one for carrying out an operation of the average value and the standard deviation of the cluster the center of which is on the estimation curve, and obtaining a frequency distribution of the cluster specified by the estimation curve.

For example, the discriminating means may enable to obtain the frequency distribution of the cluster of platelets which are distributed so as to center on the estimation curve, and the counting means enables to count the number of particles in the area (called a second area) positioned away from the estimation curve at not less than a distance of (the average value of this frequency distribution)+2×(the standard deviation). As will be described later, the particles present in the second area, the number of which is counted in relation to the cluster of platelets, have a large pulse width for their signal pulse height, and the cluster thereof is not on the estimation curve and is, therefore, a group of platelet aggregations. This has been confirmed by capturing images of the particles with the image capturing means.

FIG. 1 illustrates an optical system in one embodiment of the particle measuring apparatus according to the present invention. This embodiment has two light sources, specifically a continuous laser beam source 21 for continuously generating a laser beam to detect scattered light or fluorescence, and a pulse light source 8 for capturing images of particles. The light beams L1 and L2 from the two light sources 21 and 8 are radiated to cross each other at right angles, i. e., at 90 degrees, in such a manner that each of the light beams and the sheath flow cell 5 also meet at right angles. In FIG. 1, a sample stream flows along the direction perpendicular to the paper surface.

Figure 2:
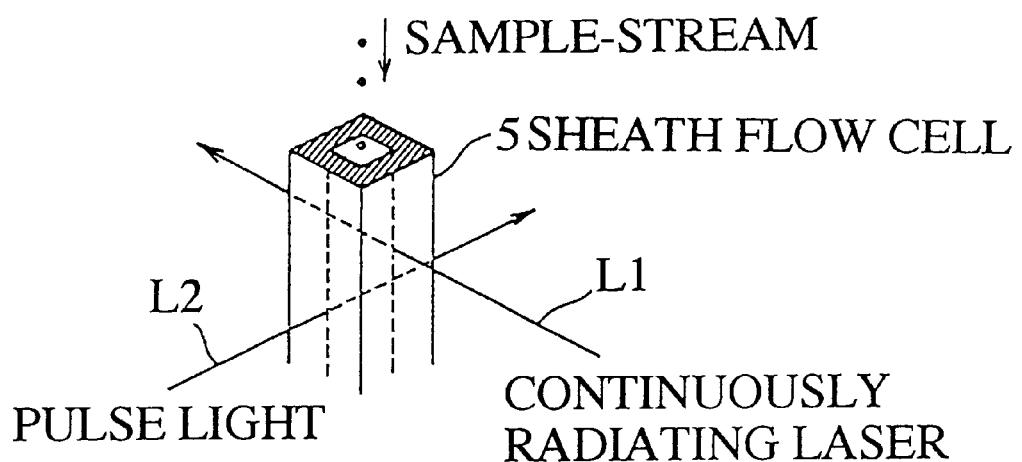
FIG. 2 shows a structure of a flow cell portion in a measuring apparatus according to the invention.

In this embodiment, the pulse light for capturing images of the particles is applied to irradiate the sample stream in the sheath flow cell 5, at the downstream of the position irradiated by the continuous laser beam source 21, the two irradiated positions being away at a distance of, e.g., about 0.5 mm, as shown in FIG. 2. Such a shift of one irradiated position from the other makes it possible to capture images of the particles clearly without any influence of scattered light or fluorescence from the cell.

The continuously emitted laser beam is made fine by a condenser lens 24 to irradiate the sample stream guided into the sheath flow cell 5. When the particles flow into this irradiated area, the scattered light and fluorescence from the particles are collected with a collecting lens 25. The scattered light is reflected by a dichroic mirror 26 and is received by a photodiode 27. Green fluorescence and red fluorescence are reflected by a dichroic mirror 28 and a mirror 29 and then received and intensified with photoelectric intensifiers 30 and 31, respectively.

The scattered light signal intensity S1 and the fluorescence signal intensities S2 and S3 detected with the photodiode 27 and the photoelectric intensifiers 30 and 31 are given to a signal processing device not shown to obtain information such as the height, area and width of the pulses of the respective detected signals, as A/D converted data.

For example, the signal processing device supplies four characteristic parameters, i.e., scattered light intensity (a), signal pulse width (b), green fluorescence intensity (c) and red fluorescence intensity (d). These parameters are used to identify the type of each of the particles in real time.

Capturing images of particles with the video camera, may be discriminately applied to only a type of the particles which is beforehand specified as a subject whose image is to be captured (e.g., a platelet). Specifically, the characteristic parameter of some particle is compared in real time with that of the type of the particle whose image is to be captured in order to examine consistency of them, and consequently if it is concluded that the particle is a subject whose image is to be captured, a luminescence trigger signal for capturing images of the particles is supplied to a pulse light source 8.

The pulse light source 8 is a light source which emits light in an instant (for about several ten nano seconds) by luminescence trigger signal Ts, and makes it possible to capture images of the flowing particles in the sample stream without any blur even if the flow speed of the sample stream is very high, e.g., several meters per second. As shown in FIG. 2, the pulse light is guided with an optical fiber 22 to the sheath flow cell 5 and is made fine by a condenser lens 23 to irradiate the sample stream. Irradiation through the optical fiber 22 causes a drop in coherency of the pulse light. The drop permits images of the particles to be captured so as to obtain the images with very few diffraction stripes. The pulse light penetrating through the sample stream is focused into an image on a receiving surface of a video camera 10 by a projecting lens 24, so as to capture transmitted light images of cells. The video signal Vs from the video camera 10 is given to an image processing device 11 to be stored and preserved as a digital image.

In the image processing device 11, the stored particle image is analyzed to extract an edge of the particle image and to calculate image parameters such as an area, a circle-equivalent diameter and a roundness of the image.

In the present invention, the pulse light source 8, the video camera 10 and the image processing device 11 are supplementary devices for capturing images of the particles and checking whether the measured particle is a platelet, a fragmented erythrocyte or a fragmented leukocyte or, further, whether the measured particle is an unnecessary particle such as a dust. Therefore, they do not directly contribute to the preparation of the two-dimensional scattergram (two-parameter scattergram) or to the separating treatment of the respective particle areas.

The characteristic parameters (a)–(d) about the intensity of scattered light, the intensity of fluorescence and the like are combined, a two-dimensional scattergram (two-parameter scattergram) is prepared and displayed, a specified type of particles is separated, and the number of the particles is calculated.

The above description is the outline of the structure of the particle measuring apparatus according to the present invention.

The following will describe the process for preparing a two-dimensional scattergram (two-parameter scattergram) using characteristic parameters, e.g., scattered light intensity, and statistically measuring the number of particles positioned away from the area of a particle cluster at a given distance or more, so as to detect aggregations of particles. In this case, the target particles are aggregations of platelets and the non-target particles are, for example, non-aggregated platelets (including reticulated platelets).

Specifically, an embodiment will be explained in which a blood sample containing platelets is used in a particle measuring apparatus according to the present invention to detect and count aggregations of platelets.

Figure 3:
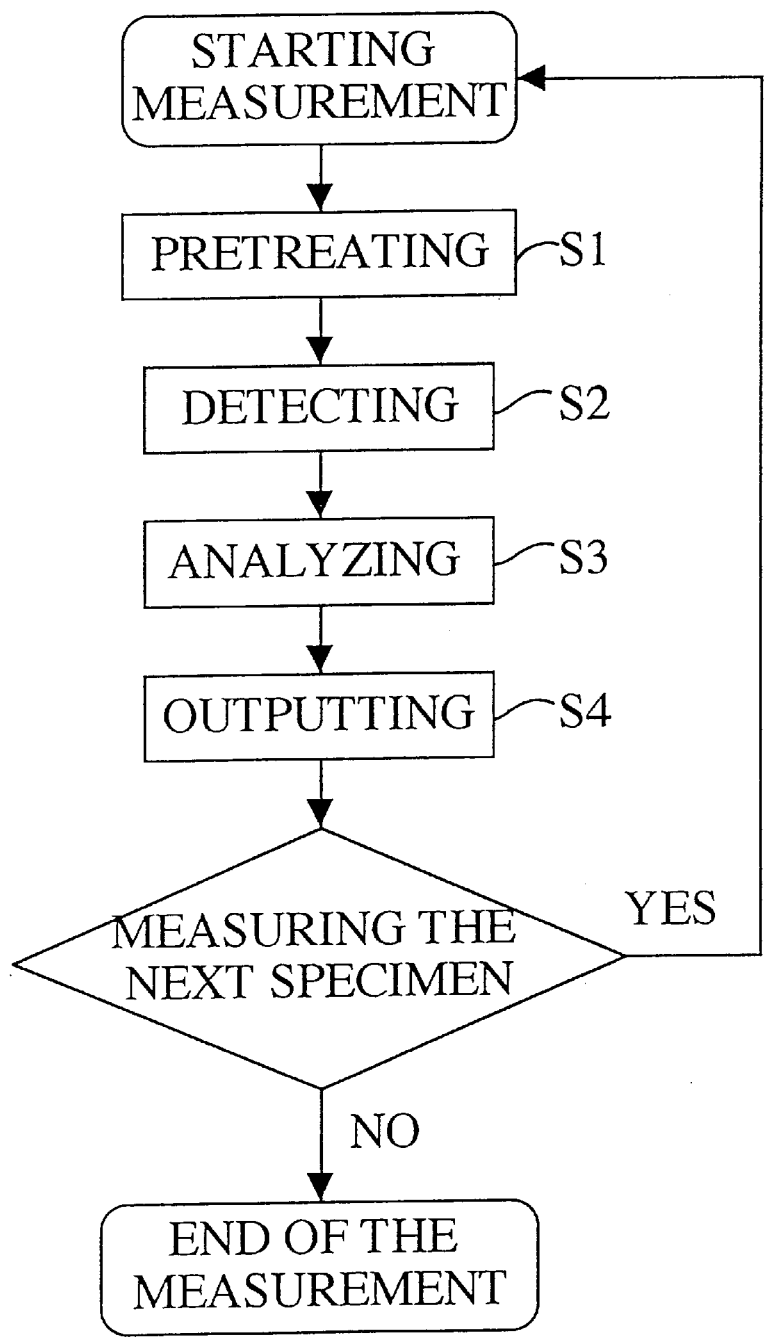
FIG. 3 shows a flowchart of detecting aggregations of platelets according to the invention.

FIG. 3 shows a flowchart of detecting aggregations of platelets according to the invention.

The process for detecting aggregations of platelets principally comprises the following four steps S1–S4.

Pretreatment S1

Two hundred microliters of a whole blood sample are sucked into the measuring apparatus according to the present invention. Ten microliters of this sample are used for measurement.

The sample for this measurement is immediately mixed with 40 $\mu$L of 2.6% Auramine O reagent solution (95.9% ethylene glycol) and 1950 $\mu$L of a buffer solution. This mixing causes platelets to be stained in a very short time.

Detecting Step S2

In a sheath flow cell, an argon ion laser beam having a wavelength of 488 nm is applied onto 2.8 $\mu$L of the sample liquid mixed and fluorescence-dyed in the pretreatment step S1.

In a photodiode and photomultiplier, the laser beam scattered by respective particles in the sample liquid is photoelectrically converted into an electric signal to measure forward scattered light intensity (FSC) and fluorescence intensity (FL).

The electric signal converted photoelectrically is sample-held at its peak value, and is A/D-converted to be supplied to a signal processing device as a characteristic parameter. Forward scattered light pulse width FSW is obtained by analyzing the information from the FSC with the passage of time.

Analyzing Step S3

Prepared are a first scattergram (A) in which its X-axis represents fluorescence intensity FL and its Y axis represents forward scattered light intensity FSC, and a second scattergram (B) in which its X axis represents forward scattered light pulse width FSW and its Y axis represents forward scattered light intensity FSC. In these scattergrams, respective particle clusters are separated, and the numbers of dots in the separated respective areas are counted to calculate, for example, a ratio of aggregation. This analyzing step will be described later.

Outputting Step S4

The results such as the ratio of aggregation calculated in the analyzing step S3, and the scattergrams are outputted into a displaying device or a printer.

The above is a flow chart according to the present invention. The four steps, i.e., S1–S4 are repeated for each of specimens to calculate, e.g., the ratio of platelet aggregation for each of the specimens. These four steps are carried out with a microcomputer in the signal processing device.

Figure 4:
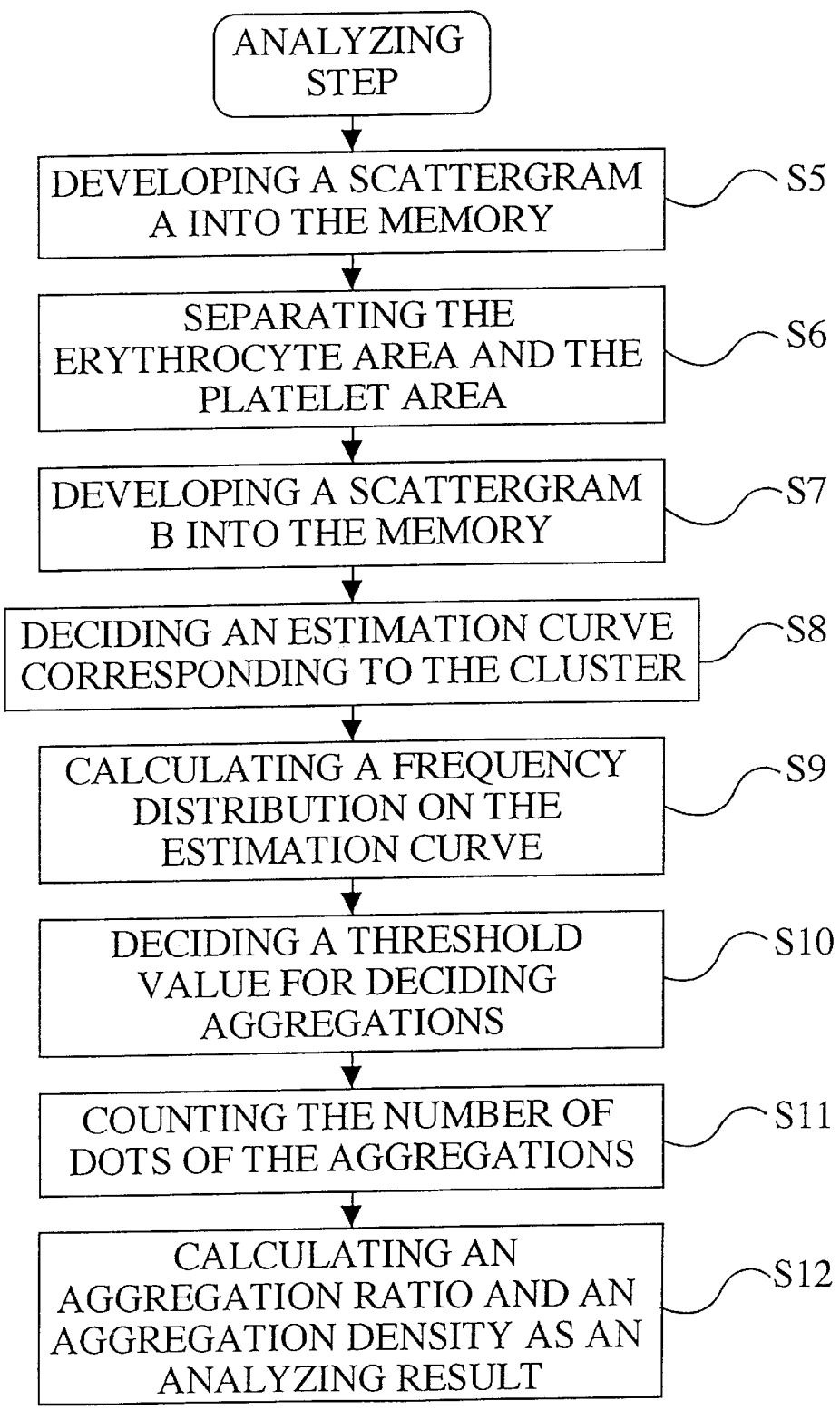
FIG. 4 shows a flowchart of the analyzing step S3 for calculating, e.g., the aggregation ratio of platelets according to the invention.

FIG. 4 shows a flowchart of the analyzing step S3 for calculating the ratio of platelet aggregation and the like.

In the signal processing device, a first scattergram (A) in which its X axis represents fluorescence intensity FL and its Y axis represents forward scattered light intensity FSC is developed and formed in the RAM (step S5).

Figure 5:
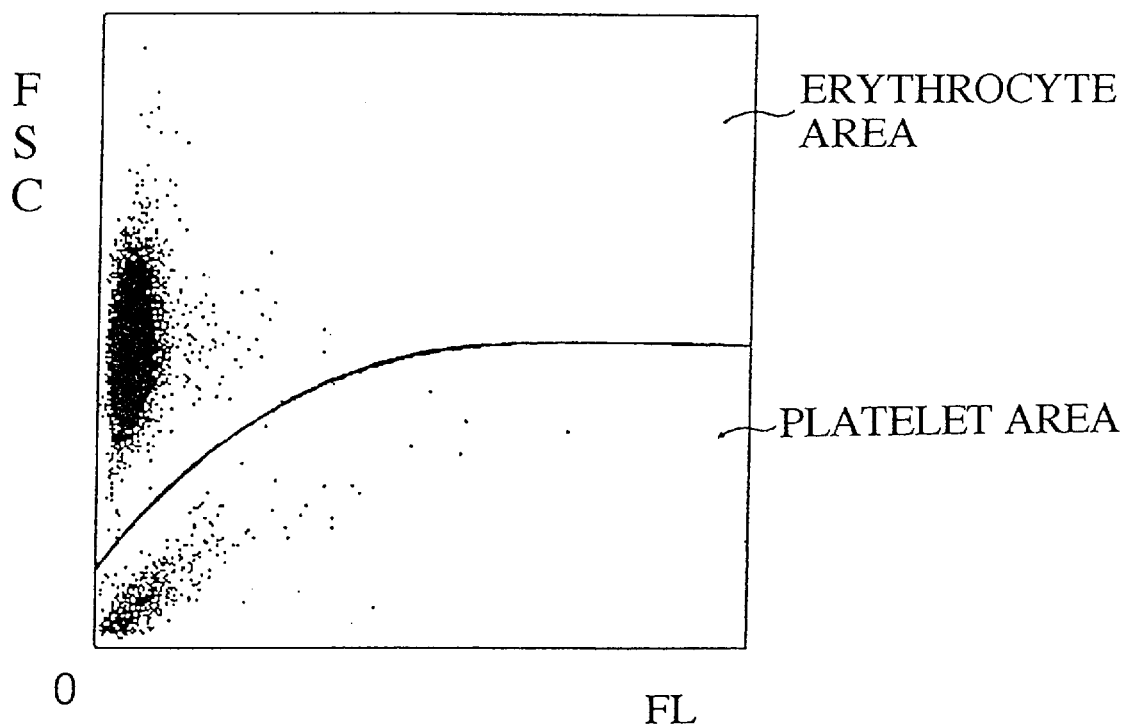
FIG. 5 shows an example of a scattergram with regard to the invention.

FIG. 5 shows an example of the first scattergram (A).

In the step S6, the first scattergram (A) is separated into an erythrocyte area and a platelet area. As a method for this separation, "the two-dimensional distribution (two-parameter distribution) separating method" may be used which is disclosed in JP-A-1-308964.

According to this method, a separating line can be drawn to separate the erythrocyte area present on the upper left part of the first scattergram (A) and the platelet area present on the lower part. The aggregations of platelets, which are the target particles, are present in the lower part of the first scattergram (A).

In the step S7, for particles in the platelet area on the lower part of the first scattergram (A), a second scattergram (B) in which its X axis represents forward scattered light pulse width FSW and its Y axis represents forward scattered light intensity FSC is developed and prepared in the RAM.

Figure 6:
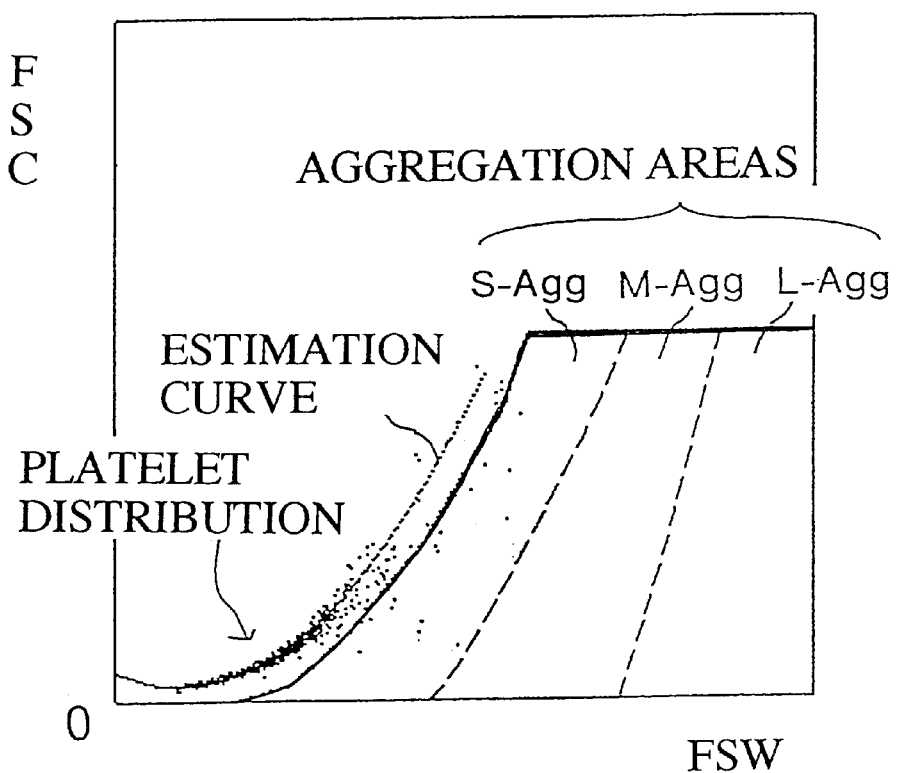
FIG. 6 shows a scattergram of the platelet area illustrated in FIG. 5.

FIG. 6 shows an example of the second scattergram (B) representing the particle distribution within the platelet area shown in FIG. 5.

According to FIG. 6, it can be understood that the distribution of most of the particles (here, non-aggregated platelets) within the platelet area is lined up on a substantially single curve. This curve is an estimation curve in this embodiment.

In the step S8, this estimation curve is approximately obtained. Specifically, the method of least squares is used to obtain a function of the curve corresponding to the distribution form of the particles. Herein, it is assumed that the estimation curve is approximated to a function of the square of a sine.

This is because in general the electric signal detected when particles pass through a flow cell is taken out as a pulse wave form and this wave form is known to be approximated to a function of the square of a sine.

When the height and the width of the pulse wave form are represented by Y and X, respectively, the relationship between the pulse height and the pulse width is shown by the following equation:

$$Y = \alpha \sin^2 X \tag{1}$$

wherein $\alpha$ is a constant, i.e., the peak value (Height) of the pulse height.

In a point $X_1$ ($0 < X_1 < \pi/2$) on the X axis, the pulse width (Width) is as follows:

$$\text{Width} = \pi - 2 X_1 \tag{2}$$

At that time, the following equation is satisfied at the discriminating position (Thresh) at $X_1$:

$$\text{Thresh} = \alpha \sin^2 X_1 \tag{3}$$

Thus, the following equation can be obtained.

$$\text{Width} = \pi - 2\sin^{-1}\sqrt{(\text{Thresh}/\alpha)} \tag{4}$$

Accordingly, the peak value (Height) of the pulse height is represented by the following equation.

$$\text{Height} = \alpha = (\text{Thresh})/\sin^2[(\pi - \text{Width})/2] \tag{5}$$

On the other hand, in the second scattergram (B), the forward scattered light intensity (FSC) of the Y axis and the forward scattered light pulse width (FSC) of the X axis correspond to the "Height" and "Width", respectively.

The estimation curve shown in FIG. 6 is drawn on the basis of the equation (5). According to FIG. 6, it can be understood that the particle distribution of the platelet area is substantially along this estimation curve but is away more and more from this estimation curve as the forward scattered light pulse width FSW becomes bigger.

This demonstrates that because platelets not aggregated usually have a symmetrical shape close to a circle, the detected electric signal from them has a pulse wave form symmetrical in the right and left portions so that the distribution thereof is along the estimation curve. On the contrary, aggregations have a large size and an asymmetrical shape, and consequently the pulse width of the electric signal from them becomes large. Therefore, as shown in FIG. 6, as the pulse width becomes larger, the particle distribution tends to be shifted more and more toward the right from the estimation curve. Namely, the aggregations are present in an area shifted away from this curve.

By capturing images of the particles accompanied by the detecting step S2, it has been additionally confirmed that the particles showing a large pulse width include aggregations.

In the next step S9, calculated is a frequency distribution of the cluster of platelets distributed on and near the estimation curve.

Specifically, the number of dots in the cluster on the estimation curve in the second scattergram (B) is accumulated, and a frequency distribution is prepared wherein its horizontal axis represents a distance from the estimation curve and its vertical axis represents the number of the dots. From this frequency distribution, the average value (AV) of this cluster and the standard deviation (SD) thereof can be obtained.

In the step S10, a threshold value for discrimination of aggregations is determined. The threshold value may be inputted by a user or may be set beforehand in, e.g., the RAM.

Herein, it is assumed that the point at a distance of [(the average value)+(the standard deviation)×2] (i.e., AV+2SD) from the frequency distribution corresponds to the threshold and the area over this threshold includes aggregations.

In the step S11, the number of the dots present in the area exceeding (AV+2SD) is counted. The counted number of the dots is defined as the number of aggregations $Agg.

In the step 12, the aggregation ratio (Agg %) and the aggregate density (Agg#) of platelets and the like are calculated.

When the total number of dots within the platelet area obtained in the scattergram A is represented by $PLT, the aggregation ratio Agg % can be obtained from the following equation.

$$Agg\ \% = \$Agg/\$PLT \times 100 \tag{6}$$

The number PLT# (the number/$\mu$L) of platelets in the whole blood can be obtained by the following equation.

$$PLT\# = \$PLT \div (\text{the volume of the analyzed sample}) \div (\text{diluting ratio}) \tag{7}$$

Furthermore, the aggregation density Agg# can be obtained by the following equation.

$$Agg\# = PLT\# \times Agg\ \% \div 100 \tag{8}$$

From the second scattergram (B) shown in FIG. 6, the respective values are obtained as follows:

$Agg=18, $PLT=1059, and

Agg %=1,7%.

In short, the number of platelet aggregations is about 1.7 percent of the total number of platelets, and in the case of PLT#=250×103 (the number/$\mu$L), about 4250 (the number/$\mu$L) aggregations are present.

It is known about the scattergram shown in FIG. 6 that, toward the right direction along the X axis, aggregations become larger.

As shown in FIG. 6, two threshold value curves are set up so as to separate the aggregation area into 3 equal parts, and the respective areas are defined as a large aggregation area L-Agg, a middle aggregation area M-Agg and a small aggregation area S-Agg. The aggregation ratios in the three areas are referred to as L-Agg %, M-Aggo and S-Agg %, respectively.

By calculating a ratio of the number of the particles in each of the respective areas to the number (Agg#) of the particles contained in the aggregation area, it is understood that L-Agg % is 0.0%, M-Agg % is 0.7%, and S-Agg % is 99.3%. for the specimen in FIG. 6.

The small aggregation area S-Agg is an area containing aggregations of about 2–4 platelets according to image capturing, and may be defined as "a feeble aggregation area". For respective specimens, therefore, feeble aggregations of platelets can be detected by obtaining the number of the particles and the aggregation ratio in the small aggregation area S-Agg in the same manner as above.

Next, an embodiment will be explained in which the particle measuring apparatus of the invention is applied to a blood sample containing platelets for correctly detecting and counting platelets. In this embodiment, the target particles are platelets (including reticulated platelets) and the non-target particles inhibiting the detection of the target particles are, for example, background noise.

The laser beam intensity in the flow cytometer shows a Gaussian distribution and the laser beam is condensed in an elliptical shape having a major axis (in the direction perpendicular to the flow) of, for example, 200 $\mu$m and a minor axis (in the direction of the flow) of, for example, 8 $\mu$m at the center of the flow cell. This is for ensuring that the irradiation intensity of the laser beam is not varied depending on the position of the particle in the sample flow.

Now, the laser beam is applied also to the sheath liquid flow existing outside of the sample flow. If dusts or air bubbles are mingled in the sheath liquid, the photodetector detects the light signal generated by these particles. Since the amount of sheath liquid flowing through the sheath flow cell is overwhelmingly larger than the amount of sample liquid, only a very small amount of particle components mingled in the sheath liquid causes a great problem. Although it is possible to employ a method in which the particle components in the sheath liquid are removed with the help of a filter, the fluid system will be complicated. Therefore, the present invention solves the problem from the view point of signal processing.

The sheath liquid and the sample liquid form a laminar flow in the flow cell, so that the particles passing near the inner wall of the flow cell have a velocity which is about one half of the flow velocity at the center. In other words, the velocity of the particles in the sheath liquid flow is slower than the velocity of the particles in the sample flow.

Because of this, the particles existing in the sheath liquid generates a signal having a large pulse width for the pulse height as compared with the particles in the sample liquid, so that it is possible to distinguish between the two.

The shot noise is generated by an electric element or an electric circuit in the apparatus, or by an external noise. Since these noise signals contain high frequency components, they have a small pulse width for the pulse height as compared with the signals from the particles. Therefore, it is possible to distinguish between the two.

Figure 7:
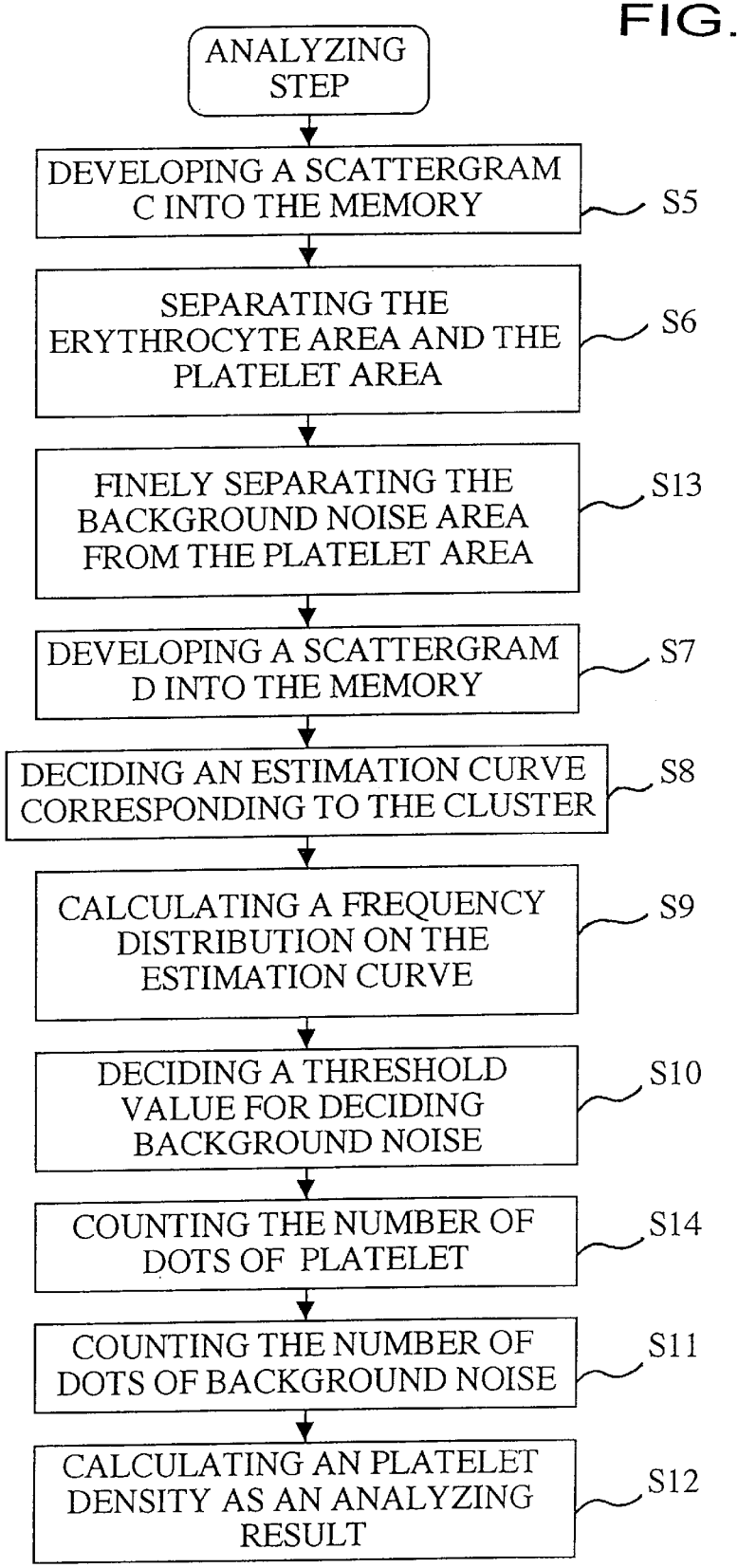
FIG. 7 shows a flowchart of the analyzing step S3 for calculating, e.g., the aggregation ratio of platelets according to the invention.

Hereafter, the analyzing process will be explained. FIG. 7 shows a flow chart for the analyzing process in this embodiment.

Figure 8A:
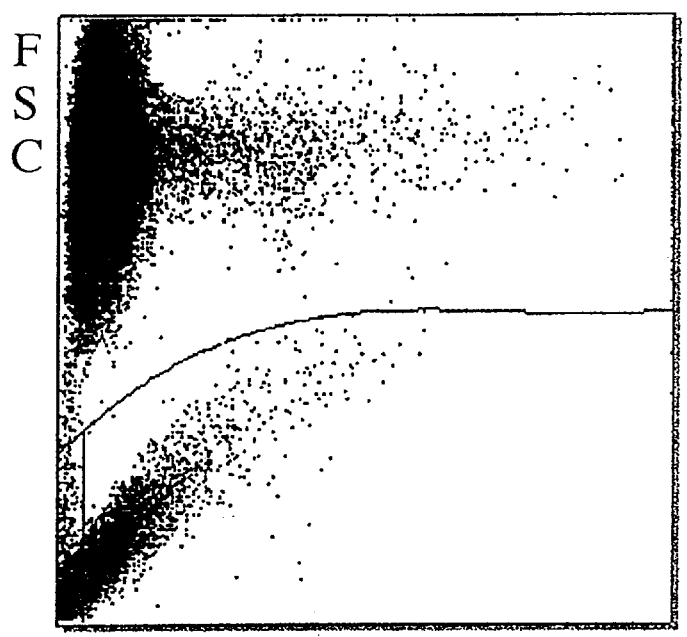
FIG. 8(a) is a scattergram (C) according to an embodiment of the invention.

First, a first scattergram (C) is prepared (step S5). FIG. 8(a) shows an example of the first scattergram (C), which has been obtained by intentionally mixing minute particle components in the sheath liquid for measurement of blood.

A fine separation of the platelet area is carried out to separate a background noise area in which background noise may possibly appear from others (step S13). In this embodiment, it was assumed that the background noise area is an area nearer to the origin in the platelet area.

Figure 8B:
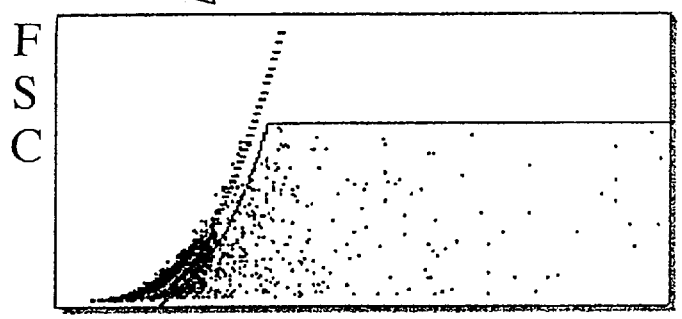
FIG. 8(b) is a scattergram (D) according to an embodiment of the invention.

Next, a second scattergram (D) is prepared for the particles in the background noise area (step S7). FIG. 8(b) shows an example of the second scattergram (D). The particles positioned away from the estimation curve are discriminated as background noise and are distinguished from the group.

The platelets flow at a high speed along the center of the flow cell, have a symmetrical shape and are distributed along the estimation curve. On the other hand, the particles in the sheath liquid flow at a low speed in the flow cell, and therefore are distributed on the right side of the estimation curve. Any noise signals having a narrow pulse width are distributed on the left side of the estimation curve.

The number of particles discriminated as background noise is counted and subtracted from the number of particles in the platelet area on the first scattergram (C) to obtain the number of platelets (step S14). When the above process of discriminating the background noise was not performed, the number of platelets was 19.0 [$\times 10^4 \mu l$]. However, when the process of discriminating the background noise was performed, the number of platelets was 16.1 [$\times 10^4 \mu l$].

The apparatus of this embodiment may be further provided with an image capturing section including a pulse laser and a video camera for image capturing, an image capture control section for operating the image capturing section, and an image processing section for processing the obtained images, wherein characteristic parameters may be extracted from particle signals obtained by the light detecting means and an image of the sample stream area may be captured on the basis of the characteristic parameters. If the pertinent particle is present in the sample stream, the particle is present in the captured image. However, if the pertinent particle is present in the sheath liquid, the particle is not present in the captured image. Therefore, the type of particle is discriminated in the image processing section according to a discrimination standard of whether a particle is present in the captured image or not.

By mounting the image capturing function and the image discriminating function, it is possible to discriminate the type of particles more accurately. Specifically, if the three characteristic parameters obtained from the particles are in the above background noise area on the scattergram (C) and correspond to the above area positioned away from the estimation curve on the scattergram (D), the image capturing device is actuated on the basis of the detection information to obtain a still image of the sample stream area. In the image processing section, the particle can be judged as a blank particle in the sheath liquid if the particle is not present in the captured image, whereas the particle can be judged as a platelet (for example, a platelet having a distorted shape) if the particle is present in the captured image.

Supposing that, for N particles present in the area positioned away from the estimation curve on the above scattergram (D), g platelets out of the captured G images were determined as platelets, it is calculated by conversion that N·g/G platelets are present in the above area. Therefore, by adding the obtained number to the number of platelets, the number of platelets can be determined more accurately.

As described above, the present invention makes it possible to count the number of target particles with good precision on the basis of the discriminating means, from a cluster of particles distributed on the distribution diagram prepared based on the characteristic parameters of the particles.

The following will describe, as an embodiment of the particle measuring apparatus according to the present invention, a process for excluding any area including substances other than platelets from the platelet area on a two-dimensional scattergram (two-parameter scattergram) and then counting the number of platelets accurately.

The present invention provides a particle measuring apparatus comprising a distribution diagram preparing means for preparing a distribution diagram of particles, a sheath flow cell for forming a fine sample stream in which the stream of the particles is surrounded by a sheath liquid, a light applying means for applying light to the sample stream, a detecting means for detecting the light obtained from the particles to which the light is applied, a calculating means for calculating characteristic parameters of the particles on the basis of the detected light, a first separating means for separating a first area containing platelets from others on the distribution diagram prepared by the distribution diagram preparing means, a second separating means for separating a second area containing fragmented erythrocytes from others within the first area, and a first counting means for counting the number of particles contained in the area in which the second area is excluded from the first area.

The second separating means may be comprised of a distribution operating means for obtaining a frequency distribution of the cluster in the first area containing platelets on the prepared distribution diagram, and a first separating line drawing means for setting up a first separating line for separating the second area containing the fragmented erythrocytes on the basis of a statistical parameter of the frequency distribution.

The particle measuring apparatus may further comprise a third separating means for separating, within the first area, a third area containing fragmented leukocytes from others, and a second counting means for excluding the number of particles in the third area from the number of particles counted by the first counting means.

The particle measuring apparatus may further comprise a fourth separating means for separating, within the first area, a fourth area containing reticulated platelets, and a third counting means for counting only the number of particles in the fourth area from the number of particles counted by the second counting means.

The fourth separating means may comprise a second separating line drawing means for setting up a second separating line for separating the fourth area containing reticulated platelets on the basis of the statistical parameter of the frequency distribution.

The distribution diagram preparing means, the separating means, the counting means, the calculating means, the first, second, third and fourth separating means, the first, second and third counting means, the first and second separating line drawing means, and the distribution operating means may be composed of a microcomputer comprising a CPU, a ROM, a RAM, a timer, an I/O interface and the like. The CPU is operated in accordance with the procedure of a program stored in, e.g., the RAM to perform the function of each of the means.

When the distribution diagram prepared by the distribution diagram preparing means is a two-dimensional scattergram (two-parameter scattergram) in which its vertical axis represents forward scattered light intensity and its horizontal axis represents fluorescence intensity, the intensity by each of the axes is represented by relative intensity (channel) to the maximum sensitivity of a photodiode, the sensitivity being 255 channels.

It has been confirmed from images captured with a flow cytometer disclosed in JP-A-8-178826 that, in this two-dimensional scattergram (two-parameter scattergram), fragmented erythrocytes appear within the first area which embraces platelets and which is separated from others by the first separating means and near the cluster of platelets, and further at the side wherein fluorescence intensity is smaller.

Because in general it is known that a healthy person does not have any fragmented erythrocyte, the second area in which the fragmented erythrocytes appear can be determined when a two-dimensional scattergram (two-parameter scattergram) for the healthy person is prepared, the first area embracing platelets is separated from others, and then the cluster of platelets is specified on the basis of a statistical parameter of the frequency distribution of the cluster.

Similarly, it is known that a healthy person does not have any fragmented leukocyte. It has been confirmed by capturing images with the flow cytometer that, if any fragmented leukocyte appears, it appears in an area wherein fluorescence intensity is considerably high, within the first area embracing platelets.

Therefore, it is possible to determine the area in which the fragmented leukocytes appear on the basis of a statistical parameter of the frequency distribution of the cluster of platelets.

It is also known that a reticulated platelet by its nature contains more nucleic acid and particle amount than a single platelet. Consequently, it has been confirmed that on a two-dimensional scattergram (two-parameter scattergram) a reticulated platelet appears in an area wherein fluorescence intensity is higher than that of the cluster of platelets.

It is also possible to determine the area embracing reticulated platelets on the basis of a statistical parameter of the frequency distribution of the cluster of platelets.

An optical system in the particle measuring apparatus for this embodiment may be the same as shown in FIG. 1.

The following will describe an embodiment comprising separating respective particle areas on a scattergram and counting the numbers of platelets, reticulated platelets and the like in the present invention.

A flowchart for counting platelets and reticulated platelets in the invention is the same as shown in FIG. 3. In other words, FIG. 3 shows a flowchart also for separating and counting platelets and the like.

Separating and counting particles such as platelets principally comprise four steps of S1 through S4. The pretreatment step S1 and the detecting step S2 may be the same as the above-mentioned ones for detecting aggregations of platelets. Thus, the explanation of these steps is omitted.

Analyzing Step S3

Prepared is a two-dimensional scattergram (two-parameter scattergram) in which its X axis represents forward fluorescence intensity FL and its Y axis represents forward scattered light intensity FSC. On this two-dimensional scattergram (two-parameter scattergram), on the basis of the characteristic parameters measured in the detecting step, respective particle clusters are separated, the number of platelets is counted, and other treatments may be conducted. The analyzing step S3 will be described in detail later.

Outputting Step S4

The result of the number of platelets calculated in the analyzing step S3 and the two-dimensional scattergram (two-parameter scattergram) are outputted into a displaying device or a printer.

The four steps, i.e., S1–S4 are repeated for each specimen, e.g., to count the number of platelets for each of the specimens.

Figure 9:
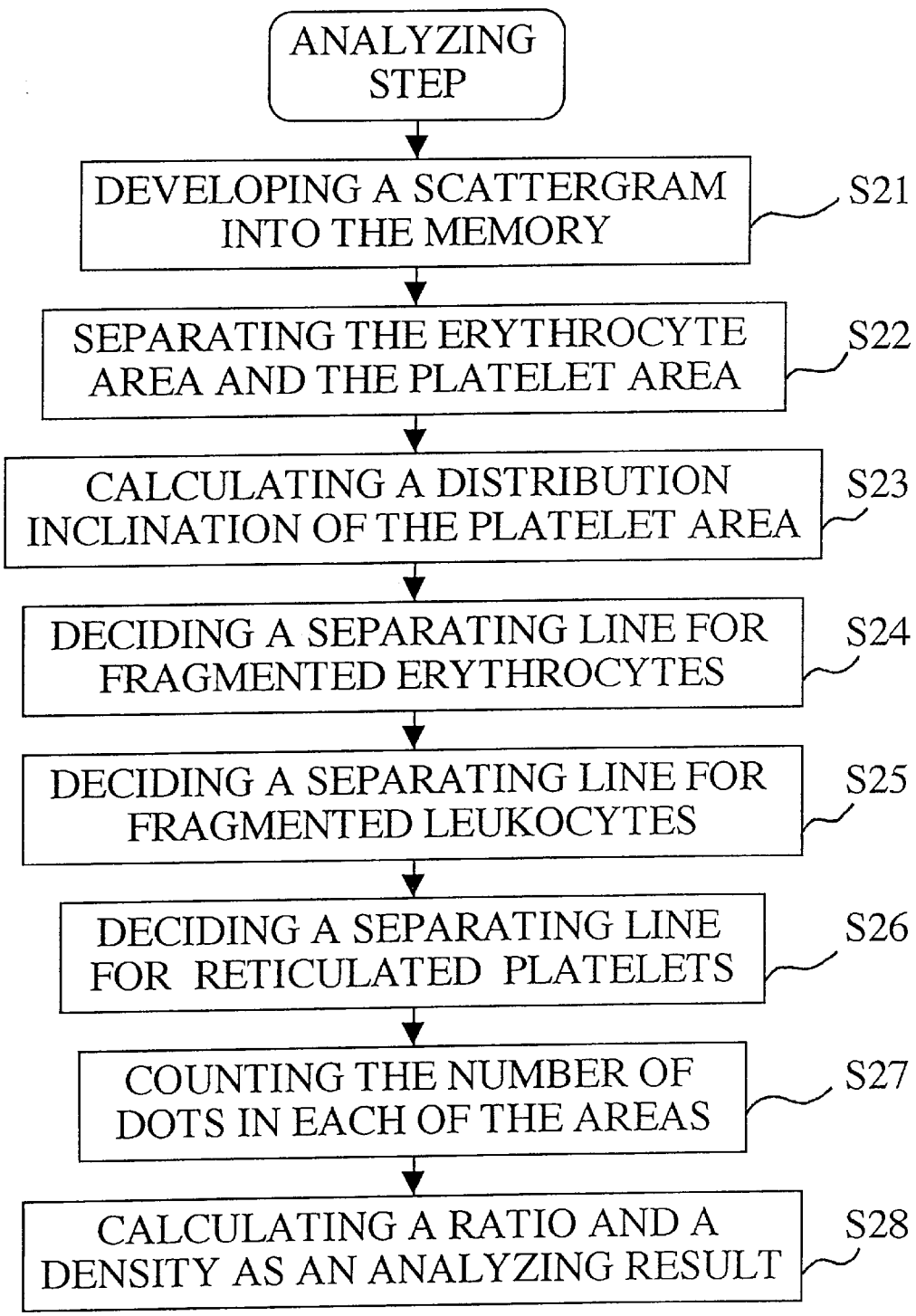
FIG. 9 shows a flowchart of the analyzing step S3 for calculating, e.g., the number of platelets according to the invention.

FIG. 9 shows a flowchart of the analyzing step S3 for counting the number of platelets and conducting other treatments.

In the signal processing device, using characteristic parameters of respective types of particles obtained in the detecting step S2, a scattergram in which its X axis represents forward fluorescence intensity FL and its Y axis represents forward scattered light intensity FSC is developed and prepared in the RAM (step S21).

Figure 10A:
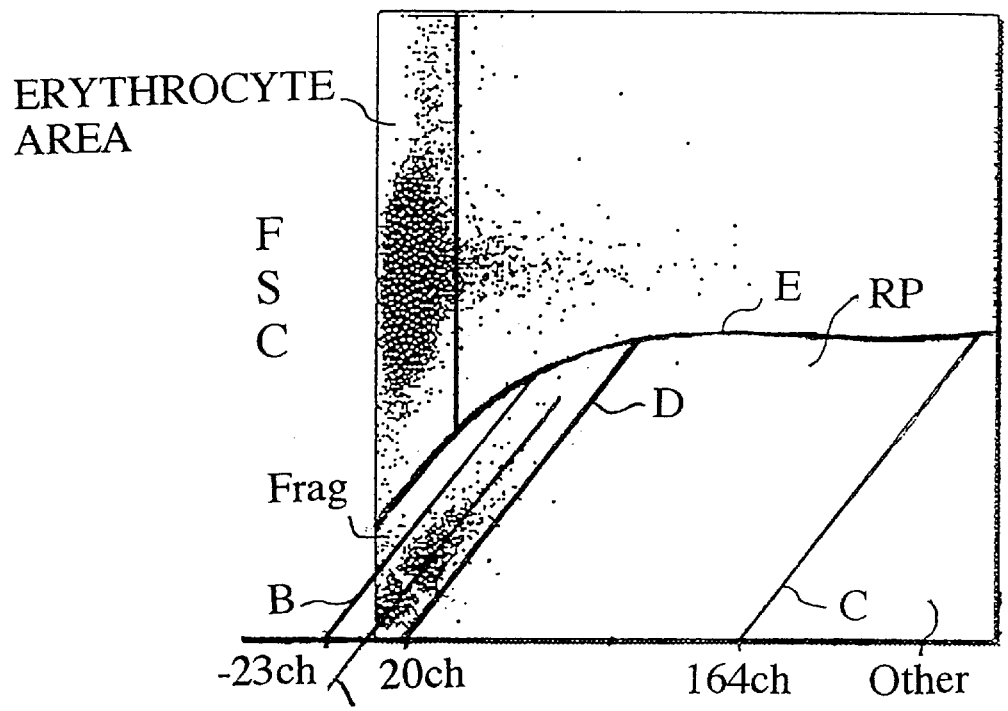
FIG. 10(a) shows an example of a scattergram with regard to the invention.

FIG. 10(a) shows an example of the scattergram.

Forward scattered light intensity of the vertical axis (Y axis) corresponds to the size of the particle.

Forward fluorescence intensity of the horizontal axis (X axis) corresponds to the RNA content.

In the step S22, the scattergram is separated into two areas: an erythrocyte area and a platelet area. As a method for the separation, the "two-dimensional distribution (two-parameter distribution) separating method" may be used which is disclosed in the above-mentioned JP-A-1-308964.

According to this method, a separating line can be drawn to separate the erythrocyte area, which is present at the upper left part on the scattergram, and the platelet area, which is present at the lower portion thereon, as shown FIG. 10(a). In FIG. 10(a), the curve (E) is the separating line.

In the step S23, the distribution angle of the platelet area is calculated.

The distribution angle is an inclination (tan θ) of the line connecting the center of gravity of a cluster of the particles to the origin on the scattergram. The line is represented by (A) in FIG. 10(a).

The center of gravity of the cluster of platelets can be obtained from the average value of scattered light intensity (FSC) and that of fluorescence intensity (FL) of respective platelets in the platelet area.

Figure 10B:
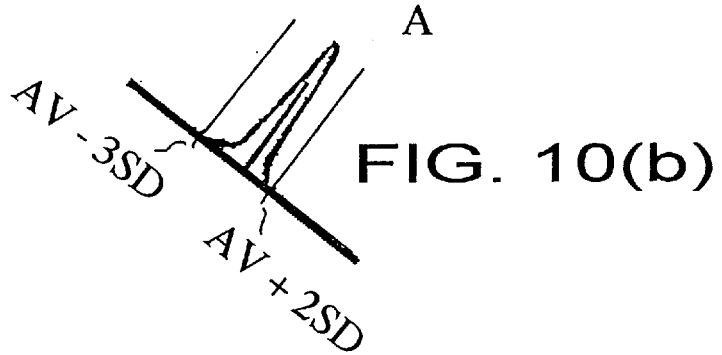
FIG. 10(b) shows a graph of a frequency distribution of particles projected in a direction perpendicular to the line (A) in FIG. 10(a).

In the step S24, a separating line for fragmented erythrocytes is determined. About a healthy person's blood containing no fragmented erythrocytes, it can be statistically estimated that, in the frequency distribution obtained from a projection in the direction perpendicular to the line connecting the center of gravity of the cluster of platelets to the origin, the cluster of platelets is within the area of [(the average value)−(the standard deviation)×3] (i.e., AV−3SD). FIG. 10(b) shows a graph of the frequency distribution of particles projected in a direction perpendicular to the line (A). By capturing images of fragmented erythrocytes, it has been confirmed that they are present in the portion exceeding (AV−3SD).

Thus, as the separating line for fragmented erythrocytes, the line is specified which is parallel to the line connecting the center of gravity of the cluster of platelets to the origin and which is at the position corresponding to (AV−3SD).

Specifically, the separating line is specified by obtaining a line with an inclination tan θ, passing at 23 channels on the X axis representing fluorescence intensity. In FIG. 10(a), the line (B) is the separating line for fragmented erythrocytes.

In FIG. 10(a), particles present in the left side area of the line (B) and within the platelet area are regarded as fragmented erythrocytes (Frag). This area in which fragmented erythrocytes are present is referred to as a "Frag area".

In the step S25, the separating line for fragmented leukocytes is decided.

It is known that fragmented leukocytes do not appear in any specimen from a healthy person but appears only in a specimen from a person who is suffering from a specific disease. It has been confirmed that, in measuring such a specimen and capturing images of the particles therein, fragmented leukocytes come into existence in the area exceeding 164 channels on the X axis showing fluorescence intensity.

Thus, a line with an inclination tan θ passing at 164 channels on the X axis is obtained, and the line is specified as the separating line for fragmented leukocytes.

In FIG. 10(a), the line (C) is this separating line. The particles present in the right side area of the line (C) and within the platelet area are regarded as fragmented leukocytes (Other). This area in which fragmented leukocytes are present is referred to as an "Other area".

The area embracing highly pure platelets is specified by the platelet area obtained through the steps S22, S24 and S25, and the separating lines (B) and (C).

In short, particles within the platelet area and outside the Frag area and Other area are specified as highly pure platelets.

In the next step S26, the separating line for reticulated platelets is determined.

It is known that a reticulated platelet has a higher fluorescence intensity than a normal, single platelet. Herein, the line at a position corresponding to [(the above-mentioned average value of the frequency distribution)+(the standard deviation)×2] (i.e., AV+2SD) is defined as the separating line for reticulated platelets.

Specifically, a line with an inclination tanθ passing at 20 channels on the X axis in the scattergram is specified as the separating line, and then platelets in the right side area of this line are regarded as reticulated platelets.

In FIG. 10(a), the line (D) is this separating line. The particles within the platelet area and within the area surrounded by the line (D) and the line (C) are regarded as reticulated platelets (RP). This area in which reticulated platelets are present is referred to as an RP area.

In the above-mentioned manner, the particles on the scattergram are separated into ones in the Frag area, the RP area, the Other area and the area for the cluster of platelets.

FIGS. 11(a) and 11(b) show examples of scattergrams of specimens containing fragmented erythrocytes.

FIG. 11(a) shows a scattergram in which the erythrocyte area and the platelet area are separated. FIG. 11(b) shows a scattergram after the Frag area is removed off from the scattergram shown in FIG. 11(a).

The area surrounded by the lines (B) and (C) within the platelet area is a highly pure platelet area.

In the next step S27, the number of particles in each of the areas is counted.

The number of the particles is obtained by counting dots, in each of the areas on the scattergram developed in the RAM, by use of the CPU.

Herein, the counted numbers of the dots in the Frag area, the RP area and the Other area are referred as $Frag, $RP and $Other, respectively.

In the step S28, from the above-mentioned counted numbers and the number ($PLT) of all the dots in the platelet area, ratios of the numbers of the particles in the respective areas to the number of all the dots in the platelet area are obtained by the following equations:

$$\text{Frag \%} = \$Frag/\$PLT \times 100 \tag{11}$$

$$RP\ \% = \$RP/\$PLT \times 100 \tag{12}$$

and $$\text{Other \%} = \$Other/\$PLT \times 100 \tag{13}$$

Frag %, RP % and Other % represent a ratio of the number of fragmented erythrocytes to the total number of platelets, a ratio of the number of reticulated platelets to the total number of platelets, and a ratio of the number of fragmented leukocytes to the total number of platelets, respectively.

Using the volume of the analyzed sample and a dilution ratio, the density PLT# (the number/$\mu L$) of platelets in the whole blood is calculated by the following equation:

$$PLT\#=\$PLT\div(\text{the volume of the analyzed sample } (\mu L))\div(\text{the dilution ratio}) \quad (14)$$

The density (Frag#) of fragmented erythrocytes in the whole blood, the density (RP#) of reticulated platelets therein, and the density (Other#) of fragmented leukocytes therein are respectively calculated by the following equations.

$$\text{Frag}\#=PLT\#\times\text{Frag }\%\div100 \quad (15)$$

$$RP\#=PLT\#\times RP\text{ }\%\div100 \quad (16)$$

$$\text{Other}\#=PLT\#\times\text{Other }\%\div100 \quad (17)$$

The number (P-PLT#) of highly pure platelets, which exclude fragmented erythrocytes and fragmented leukocytes, is obtained by the following equation.

$$P\text{-}PLT\#=PLT\#-\text{Frag}\#-\text{Other}\# \quad (18)$$

About the specimen shown in FIGS. 11(a) and 11(b), respective calculated values obtained by conducting an analyzing process according to the present invention are as follows.

$PLT=1059$ (dots)

$\#PLT=195\times10^3$ (the number/$\mu L$)

RP %=0.27 (%)

Frag %=0.5%,

Other %=0.0%, $RP\#=0.53\times10^3$ (the number/$\mu L$)

$\text{Frag}\#=0.98\times10^3$ (the number/$\mu L$)

$\text{Other}\#=0.0$ (the number/$\mu L$)

$P\text{-}PLT\#=194\times10^3$ (the number/$\mu L$)

Such analysis as above makes it possible to count the number (P-PLT#) of highly pure platelets, and calculate the number (RP#) of reticulated platelets.

According to the present invention, the number of platelets can be counted accurately because a separating line is drawn on a scattergram to separate areas in which given particles are present and particles other than platelets, such as fragmented erythrocytes, are removed off from the particles in the platelet area.

What is claimed is:

1. A particle measuring apparatus comprising:

characteristic parameter extracting means for extracting a plurality of characteristic parameters from each particle in a sample;

distribution diagram preparing means for preparing at least one first distribution diagram on the basis of the extracted characteristic parameters;

first separating means for separating a cluster including target particles from other information on the prepared at least one distribution diagram;

discriminating means for calculating a discrimination function for the separated cluster including the target particles and for discriminating target particles from non-target particles in the cluster on the basis of a distance from the calculated discrimination function; and counting means for counting the number of the target particles discriminated by the discriminating means.

2. A particle measuring apparatus according to claim 1, further comprising a second separating means for finely separating the cluster including the target particles into a plurality of clusters on the first distribution diagram, wherein the distribution diagram preparing means prepares a second distribution diagram for each of the finely separated clusters, and the discriminating means calculates a discrimination function for at least one cluster among the plurality of clusters.

3. A particle measuring apparatus according to claim 2, wherein the discrimination function is prepared based upon the second distribution diagram, and the discriminating means discriminates a particle type on the basis of distance from the discrimination function.

4. A particle measuring apparatus according to claim 3, wherein the discriminating means discriminates the particles positioned at least a given distance from the discrimination function as the target particles.

5. A particle measuring apparatus according to claim 3, wherein the discriminating means discriminates the particles positioned at least a given distance from the discrimination function as the non-target particles.

6. A particle measuring apparatus according to claim 1, further comprising an image capturing section, an image capture controlling section and an image processing section, wherein the image capture controlling section operates the image capturing section for each particle in a cluster including the target particles on the basis of the extracted characteristic parameters of the particles, the image processing section processes the image obtained by the image capturing section to detect a presence or absence of a particle in the image, and the discriminating means discriminates whether the particle is a target particle or a non-target particle based on a presence or absence detected in the image processing section.

7. A particle measuring apparatus according to claim 4, wherein the target particles are aggregations of platelets.

8. A particle measuring apparatus according to claim 5, wherein the target particles are platelets and the non-target particles are background noise.

9. A particle measuring apparatus according to claim 1, wherein the characteristic parameter extracting means comprises a sheath flow cell for forming a fine sample stream in which a sample liquid containing the particles is surrounded by a sheath liquid, a light applying means for applying light to the sample liquid made into the fine stream, a detecting means for detecting the light scattered by the particles to output electric signals, and a calculating means for calculating the characteristic parameters of the particles from the detected light.

10. A particle measuring apparatus according to claim 1, further comprising a second separating means for finely separating the cluster including the target particles into a plurality of clusters on the first distribution diagram, the discriminating means discriminating one of the plurality of clusters as the non-target particles.

11. A particle measuring apparatus according to claim 10, wherein the first separating means separates a first area containing platelets as the target particles from other information on the first distribution diagram, the second separating means separates a second area containing fragmented erythrocytes from other information within the first area, and the counting means counts the number of particles contained in the first areas, excluding the second area, as the number of platelets.

12. A particle measuring apparatus according to claim 11, wherein the second separating means is comprised of a distribution operating means for obtaining a frequency distribution of the cluster in the first area containing platelets on the prepared distribution diagram, and a first separating line drawing means for setting up a first separating line for separating the second area containing fragmented erythrocytes on a statistical parameter of the frequency distribution.

13. A particle measuring apparatus according to claim 11, further comprising a third separating means for separating, within the first area, a third area containing fragmented leukocytes from other information, and a second counting means for excluding the number of the particles present in the third area from the number of the particles counted by the first counting means.

14. A particle measuring apparatus according to claim 13, further comprising a fourth separating means for separating, within the first area, a fourth area containing reticulated platelets from other information, and a third counting means for counting only the number of the particles present in the fourth area from the number of the particles counted by the second counting means.

15. A particle measuring apparatus according to claim 14, wherein the fourth separating means comprises a second separating line drawing means for setting up a second separating line for separating the fourth area containing reticulated platelets on the basis of the statistical parameter of the frequency distribution.

16. A particle measuring apparatus according to claim 1, wherein the discrimination function is an estimation curve.

17. A particle measuring apparatus according to claim 16, further comprising a second separating means for finely separating the cluster including the target particles into a plurality of clusters on the first distribution diagram, wherein the distribution diagram preparing means prepares a second distribution diagram for each of the finely separated clusters, and the discriminating means calculates the estimation curve for at least one cluster among the plurality of clusters.

18. A particle measuring apparatus according to claim 17, wherein the estimation curve is prepared based upon the second distribution diagram, and the discriminating means discriminates a particle type on the basis of distance from the estimation curve.

19. A particle measuring apparatus according to claim 18, wherein the discriminating means discriminates the particles positioned at least a given distance from the estimation curve as the target particles.

20. A particle measuring apparatus according to claim 18, wherein the discriminating means discriminates the particles positioned at least a given distance from the estimation curve as the non-target particles.

21. A particle measuring apparatus according to claim 1, wherein the target particles are aggregations of platelets.

22. A particle measuring apparatus comprising:
characteristic parameter extracting means for extracting a plurality of characteristic parameters from each particle in a sample;
distribution diagram preparing means for preparing at least one distribution diagram on the basis of the extracted characteristic parameters;
first separating means for separating a cluster including target particles from other information on the prepared at least one distribution diagram;
discriminating means for setting a specified discrimination standard for the separated cluster including the target particles and for discriminating target particles from non-target particles in the cluster on the basis of the discrimination standard; and
counting means for counting the number of the target particles discriminated by the discriminating means, wherein the target particles are platelets and the non-target particles are background noise.

23. The particle measuring apparatus of claim 22, wherein the distribution diagram preparing means prepares a second distribution diagram on the basis of the separated cluster, and the discrimination means sets the specified discrimination standard as a function on the second distribution diagram.

24. The particle measuring apparatus of claim 23, wherein the discrimination means discriminates the platelets from the background noise based upon distance from the function.

25. The particle measuring apparatus of claim 23, wherein the function is an estimation curve.

26. The particle measuring apparatus of claim 24, wherein the function is an estimation curve.

27. The particle measuring apparatus of claim 23, wherein the discriminating means discriminates the particles positioned at least a given distance from the function as background noise.

28. The particle measuring apparatus of claim 24, wherein the discriminating means discriminates the particles positioned at least a given distance from the function as background noise.

29. The particle measuring apparatus of claim 25, wherein the discriminating means discriminates the particles positioned at least a given distance from the function as background noise.

30. The particle measuring apparatus of claim 26, wherein the discriminating means discriminates the particles positioned at least a given distance from the function as background noise.

31. A particle measuring apparatus comprising:
characteristic parameter extracting means for extracting a plurality of characteristic parameters from each particle in a sample;
distribution diagram preparing means for preparing a first distribution diagram on the basis of the extracted characteristic parameters;
first separating means for separating a cluster including target particles from other information on the prepared first distribution diagram;
second separating means for finely separating the cluster including target particles into a plurality of clusters on the first distribution diagram;
discriminating means for setting a specified discrimination standard for the separated cluster including the target particles and for discriminating target particles from non-target particles in the plurality of clusters on the basis of the discrimination standard and discriminating one of the plurality of clusters as non-target particles; and
counting means for counting the number of the target particles discriminated by the discriminating means.

32. A particle measuring apparatus according to claim 31, wherein the first separating means separates a first area containing platelets as the target particles from other information on the first distribution diagram, the second separating means separates a second area containing fragmented erythrocytes from other information within the first area, and the counting means counts the number of particles contained in the first area, excluding the second area, as the number of platelets.

33. A particle measuring apparatus according to claim 32, wherein the second separating means is comprised of a distribution operating means for obtaining a frequency distribution of the cluster in the first area containing platelets on the prepared distribution diagram, and a first separating line drawing means for setting up a first separating line for separating the second area containing fragmented erythrocytes on a statistical parameter of the frequency distribution.

34. A particle measuring apparatus according to claim 32, further comprising a third separating means for separating, within the first area, a third area containing fragmented leukocytes from other information, and a second counting means for excluding the number of the particles present in the third area from the number of the particles counted by the first counting means.

35. A particle measuring apparatus according to claim 34, further comprising a fourth separating means for separating, within the first area, a fourth area containing reticulated platelets from other information, and a third counting means for counting only the number of the particles present in the fourth area from the number of the particles counted by the second counting means.

36. A particle measuring apparatus according to claim 35, wherein the fourth separating means comprises a second separating line drawing means for setting up a second separating line for separating the fourth area containing reticulated platelets on the basis of the statistical parameter of the frequency distribution.

* * * * *